US012603427B2

(12) United States Patent
Bosua

(10) Patent No.: US 12,603,427 B2
(45) Date of Patent: Apr. 14, 2026

(54) SHAPE CHANGING ANTENNA AND METHOD FOR USE THEREOF

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 997 days.

(21) Appl. No.: 17/584,822

(22) Filed: Jan. 26, 2022

(65) Prior Publication Data

US 2023/0238695 A1      Jul. 27, 2023

(51) Int. Cl.
*H01Q 3/01*      (2006.01)
*A61B 5/0507*      (2021.01)
*A61B 5/145*      (2006.01)

(52) U.S. Cl.
CPC ............. *H01Q 3/01* (2013.01); *A61B 5/0507* (2013.01); *A61B 5/14546* (2013.01)

(58) Field of Classification Search
CPC ...... H01Q 1/01; A61B 5/0507; A61B 5/14546
See application file for complete search history.

(56) References Cited

U.S. PATENT DOCUMENTS

| | | | |
|---|---|---|---|
| 7,068,237 B2 | 6/2006 | Fukuda | |
| 10,617,296 B2 | 4/2020 | Sloan et al. | |
| 10,856,766 B2 | 12/2020 | Leabman | |
| 10,912,500 B2 | 2/2021 | Poeze et al. | |
| 10,956,950 B2 | 3/2021 | Al-Ali et al. | |

| | | | |
|---|---|---|---|
| 11,063,373 B1* | 7/2021 | Bosua | ..................... H01Q 21/28 |
| 11,202,582 B2 | 12/2021 | Verkruijsse et al. | |
| 11,244,753 B2 | 2/2022 | Haggerty et al. | |
| 11,291,374 B2 | 4/2022 | Lee et al. | |
| 11,298,037 B2 | 4/2022 | Leabman | |
| 11,350,830 B2 | 6/2022 | Mckenna et al. | |
| 11,360,188 B2 | 6/2022 | Leabman | |
| 11,367,525 B2 | 6/2022 | Addison et al. | |
| 11,389,091 B2* | 7/2022 | Bosua | ................ A61B 5/14532 |
| 11,389,093 B2 | 7/2022 | Triman et al. | |

(Continued)

FOREIGN PATENT DOCUMENTS

| | | | |
|---|---|---|---|
| EP | 3146898 B1 | 11/2018 | |
| EP | 3981329 A1 | 4/2022 | |

(Continued)

OTHER PUBLICATIONS

Ruiz, R. et al., "A flexible dipole antenna for direct transduction of microwave radiated power into DC mechanical deflection," Sensors and Actuators: A. Physical 340 (2022) 113536, 7 pages.

*Primary Examiner* — Graham P Smith

(74) *Attorney, Agent, or Firm* — HSML P.C.

(57)      ABSTRACT

An antenna includes a controllable conductive material that is used to form transmit and/or receive antennas in different, controllable shapes. The controllable conductive material can be manipulated by an actuation control to form a continuous shape from one electrode to another to form the antenna. The controllable conductive material can be formed into multiple antennae each having a continuous shape extending between different electrodes. The antenna can be used for transmitting and receiving electromagnetic signals for determining the presence and/or amount of one or more analytes.

6 Claims, 5 Drawing Sheets

(56)     References Cited

U.S. PATENT DOCUMENTS

| | | | |
|---|---|---|---|
| 11,426,104 | B2 | 8/2022 | Schurman et al. |
| 11,510,597 | B2 * | 11/2022 | Bosua .................. A61B 5/0004 |
| 11,696,698 | B1 * | 7/2023 | Bosua ................ A61B 5/14532 |
| | | | 600/430 |
| 2009/0284416 | A1 | 11/2009 | Quinn et al. |
| 2019/0269853 | A1 | 9/2019 | Doyle et al. |
| 2020/0054255 | A1 | 2/2020 | Conrad et al. |
| 2020/0193326 | A1 | 6/2020 | Leabman |
| 2022/0015695 | A1 | 1/2022 | Margarito et al. |
| 2022/0031254 | A1 | 2/2022 | Al-Ali et al. |
| 2022/0192494 | A1 | 6/2022 | Leabman |
| 2022/0192531 | A1 | 6/2022 | Leabman |
| 2022/0248984 | A1 | 8/2022 | Poeze et al. |

FOREIGN PATENT DOCUMENTS

| | | | |
|---|---|---|---|
| WO | 2019217461 | | 11/2019 |
| WO | 2021198045 | A1 | 10/2021 |
| WO | 2022026623 | A1 | 2/2022 |

* cited by examiner

96

SHAPE CHANGING ANTENNA AND METHOD FOR USE THEREOF

FIELD

This disclosure is directed to a shape changing antenna and use of the shape changing antenna in detection of analytes.

BACKGROUND

There is interest in being able to detect and/or measure an analyte within a target. One example is measuring glucose in biological tissue. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological tissues. However, many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure is directed to a shape changing antenna and use of the shape changing antenna in detection of analytes.

Using a controllable conductive material that can be reconfigured into different shapes, a shape changing antenna capable of providing highly differentiated antenna shapes can be realized. These differentiated antenna shapes can provide antennas for use in the detection of analytes. In embodiments, the differentiated antenna shapes can be selected and tuned for detection of particular analytes or the detection of analytes in particular media.

In an embodiment, a configurable antenna includes a plurality of electrodes configured to be connected to a transmit circuit or a receive circuit, a controllable conductive material, and an actuation control. The actuation control is configured to manipulate at least some of the controllable conductive material to form a first continuous shape extending from one electrode of the plurality of electrodes to another electrode of the plurality of electrodes. The first continuous shape is configured to transmit a signal received from the transmit circuit or obtain a received signal.

In an embodiment, the configurable antenna includes a plurality of pixels each containing the controllable conductive material. In an embodiment, the plurality of electrodes includes a first set of the electrodes configured to be electrically connected to the transmit circuit and a second set of the electrodes configured to be electrically connected to the receive circuit. In an embodiment, the first continuous shape extends from one electrode of the first set of electrodes to another electrode of the first set of electrodes, the first continuous shape is configured to transmit the signal received from the transmit circuit, the actuation control is configured to manipulate some of the controllable conductive material into a second continuous shape, the second continuous shape extending from one electrode of the second set of electrodes to another electrode of the second set of electrodes, and the second continuous shape is configured to obtain the received signal to be conveyed to the receive circuit. In an embodiment, the first continuous shape and the second continuous shape do not intersect one another. In an embodiment, the configurable antenna further includes a controller configured to determine the first continuous shape and direct the actuation control to manipulate the at least some of the controllable conductive material.

In an embodiment, a non-invasive sensor system includes a controllable antenna configured to form a transmit shape and to form a receive shape, the controllable antenna configured to transmit a signal into a target using the transmit shape and to obtain a receive signal using the receive shape. In an embodiment, the controllable antenna is configured to provide the transmit shape during a first period of time and the receive shape during a second period of time. In an embodiment, the first period of time overlaps with the second period of time. In an embodiment, the first period of time does not overlap with the second period of time. In an embodiment, the second period of time begins when the first period of time ends. In an embodiment, the controllable antenna is configured to switch between the transmit shape and the receive shape.

In an embodiment, a method of analyte detection includes arranging at least some of a controllable conductive material to form a first antenna configured to transmit a transmit signal or obtain a receive signal, the first antenna including a first continuous shape from a first electrode to a second electrode. In an embodiment, the first antenna is configured to transmit the transmit signal and the method further includes transmitting the signal using the first antenna and obtaining the receive signal at a fixed antenna. In an embodiment, the first antenna is configured to obtain the receive signal and the method further includes transmitting the signal using a fixed antenna, and obtaining the receive signal at the first antenna. In an embodiment, the first antenna is configured to transmit the transmit signal, and the method further includes arranging at least some of a controllable conductive material to form a second antenna configured to obtain the receive signal, the second antenna including a second continuous shape from a third electrode to a fourth electrode. In an embodiment, the arranging of the at least some of the controllable conductive material to form the first antenna and the arranging of the at least some of the controllable conductive material to form the second antenna are performed sequentially. In an embodiment, the first antenna and the second antenna are less than 95% coupled to one another. In an embodiment, the method further includes determining an effectiveness for the first continuous shape of the first antenna. In an embodiment, the method further includes selecting a shape for use as the first continuous shape based on the determined effectiveness.

DRAWINGS

DETAILED DESCRIPTION

Figure 1:
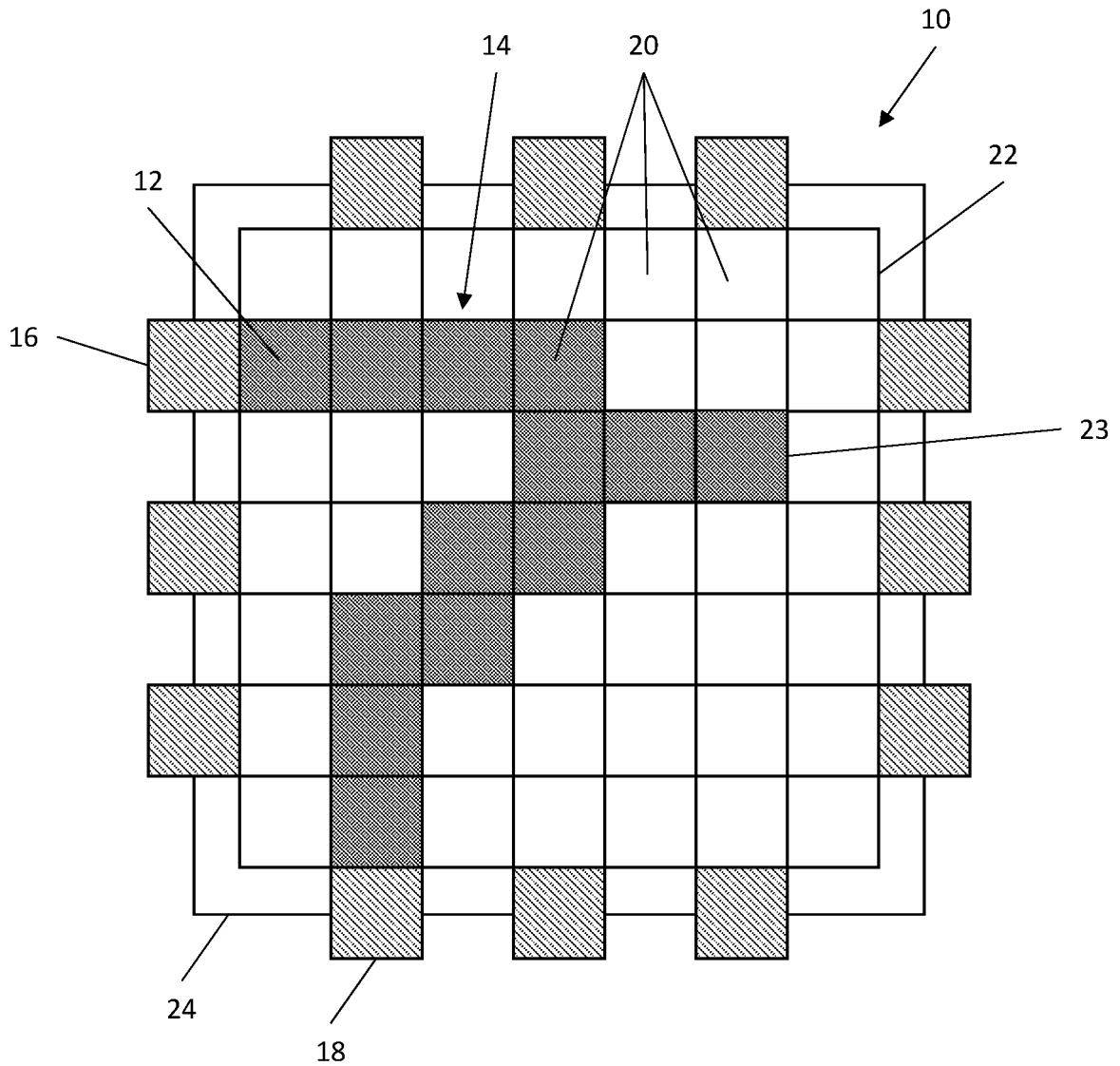
FIG. 1 shows a schematic of an antenna according to an embodiment.

This disclosure is directed to a shape changing antenna and use of the shape changing antenna in detection of analytes.

The following is a detailed description of apparatus, systems and methods of non-invasively detecting an analyte via spectroscopic techniques using non-optical frequencies such as in the radio or microwave frequency bands of the electromagnetic spectrum. A non-invasive analyte sensor includes a transmit antenna (which may also be referred to as a transmit element) that functions to transmit a generated transmit signal that is in a radio or microwave frequency range of the electromagnetic spectrum into a target containing an analyte of interest, and a receive antenna (which may also be referred to as a receive element) that functions to detect a response resulting from transmission of the transmit signal by the transmit antenna into the target. The transmit antenna and the receive antenna can have controllable shapes selected such that the transmit and receive antennae are decoupled from one another to improve the detection performance of the sensor in situations where the receive antenna is formed while the transmit antenna is being used to transmit a signal.

The transmit antenna and the receive antenna can be located near the target and operated as further described herein to assist in detecting at least one analyte in the target. The transmit antenna transmits a signal, which has at least two frequencies in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna can be decoupled (which may also be referred to as detuned or the like) from one another if the receive antenna is present when the transmit antenna is being used to transmit a signal. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. An example of detecting an analyte using a non-invasive spectroscopy sensor operating in the radio or microwave frequency range of the electromagnetic spectrum is described in WO 2019/217461, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

In one embodiment, the sensor described herein can be used to detect the presence of at least one analyte in a target. In another embodiment, the sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, or a microbe. Further non-limiting examples of targets include material or samples thereof contained within a vessel or other container.

The analyte(s) can be any analyte that one may wish to detect. The analyte can be human or non-human, animal or non-animal, biological or non-biological. For example, the analyte(s) can include, but is not limited to, one or more of blood glucose, blood alcohol, white blood cells, or luteinizing hormone. The analyte(s) can include, but is not limited to, a chemical, a combination of chemicals, a virus, bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; gluta-thione; glutathione perioxidase; glycocholic acid; glycosy-lated hemoglobin; halofantrine; hemoglobin variants; hexosaminidase A; human erythrocyte carbonic anhydrase I; 17-alpha-hydroxyprogesterone; hypoxanthine phosphoribo-syl transferase; immunoreactive trypsin; lactate; lead; lipo-proteins ((a), B/A-1, β); lysozyme; mefloquine; netilmicin; phenobarbitone; phenytoin; phytanic/pristanic acid; proges-terone; prolactin; prolidase; purine nucleoside phosphory-lase; quinine; reverse tri-iodothyronine (rT3); selenium; serum pancreatic lipase; sissomicin; somatomedin C; spe-cific antibodies (adenovirus, anti-nuclear antibody, anti-zeta antibody, arbovirus, Aujeszky's disease virus, dengue virus, *Dracunculus medinensis, Echinococcus granulosus, Enta-moeba histolytica*, enterovirus, *Giardia duodenalisa, Heli-cobacter pylori*, hepatitis B virus, herpes virus, HIV-1, IgE (atopic disease), influenza virus, *Leishmania donovani*, lep-tospira, measles/mumps/rubella, *Mycobacterium leprae, Mycoplasma pneumoniae*, Myoglobin, *Onchocerca volvu-lus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succiny-lacetone; sulfadoxine; theophylline; thyrotropin (TSH); thy-roxine (T4); thyroxine-binding globulin; trace elements; transferrin; UDP-galactose-4-epimerase; urea; uroporphy-rinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol or other alcohols; ketones; cannabis (mari-juana, tetrahydrocannabinol, hashish); inhalants (nitrous oxide, amyl nitrite, butyl nitrite, chlorohydrocarbons, hydro-carbons); cocaine (crack cocaine); stimulants (amphet-amines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocy-bin); narcotics (heroin, codeine, morphine, opium, meperi-dine, Percocet, Percodan, Tussionex, Fentanyl, Darvon, Talwin, Lomotil); designer drugs (analogs of fentanyl, meperidine, amphetamines, methamphetamines, and phen-cyclidine, for example, Ecstasy); anabolic steroids; and nicotine. The analyte(s) can include other drugs or pharma-ceutical compositions. The analyte(s) can include neuro-chemicals or other chemicals generated within the body, such as, for example, ascorbic acid, uric acid, dopamine, noradrenaline, 3-methoxytyramine (3MT), 3,4-Dihydroxy-phenylacetic acid (DOPAC), Homovanillic acid (HVA), 5-Hydroxytryptamine (5HT), and 5-Hydroxyindoleacetic acid (FHIAA).

FIG. 1 shows a schematic of an antenna according to an embodiment. Antenna 10 includes controllable conductive material 12 arranged to form a continuous shape 14 extend-ing from a first electrode 16 to a second electrode 18. In the embodiment shown in FIG. 1, the shape 14 is defined using a plurality of pixels 20 in an array 22, with first electrode 16 and second electrode 18 each being connected to a circuit such that the antenna 10 can be used to transmit or receive and analyze a signal. Actuation control 24 can be used to arrange the controllable conductive material 12 into the continuous shape 14.

Antenna 10 forms an antenna to be used for transmitting and/or receiving a signal. In an embodiment, antenna 10 can be electrically connected to a transmit circuit by first elec-trode 16 and second electrode 18, with the transmit circuit configured to generate a signal for transmission by antenna 10. In an embodiment, antenna 10 can be electrically con-nected to a receive circuit by the first electrode 16 and the second electrode 18, with the receive circuit configured to receive and analyze an electromagnetic signal acting on antenna 10. In an embodiment, the signal generated or received by antenna 10 can be in the radio or microwave frequency range. In an embodiment, the signal generated or received by antenna 10 can be between about 10 kHz to about 100 GHz.

Controllable conductive material 12 can be any suitable conductive material that can be controlled to alter a shape or position of a resulting conductive structure. The controllable conductive material 12 can be material capable of flowing into different configurations, such as a liquid, a semi-solid, gels, colloids, dispersions, powered materials, materials having plasticity, combinations thereof, and the like. The controllable conductive material 12 can conduct electricity through a length of the material. In an embodiment, the entire controllable conductive material 12 is conductive. In an embodiment, the controllable conductive material 12 includes non-conductive and conductive components, with the conductive components being sufficient for conduction of electricity through the controllable conductive material 12. Examples can include, for example, electrophoretic inks, liquid metals, or the like. In an embodiment, the controllable conductive material can include gold or platinum. Control-lable conductive material 12 can be configured into a shape by any suitable actuation control 24 for that controllable conductive material, such as emitters applying electromag-netic fields, mechanical actuators, sources of sound, or the like. Examples of shape-changing antennas are described in U.S. Pat. No. 7,068,237 and U.S. Patent Application Pub. No. 2009/0284416, which are herein incorporated by refer-ence.

Continuous shape 14 is a shape formed by control of controllable conductive material 12 to provide an electrical connection between first electrode 16 and second electrode 18. Continuous shape 14 can further be arranged such that it does not cross over any other separate configurations of the controllable conductive material, such as another antenna that is formed on array 22. Continuous shape 14 can be configured such that it does not contact any electrode provided on or near array 22 aside from first electrode 16 and second electrode 18. Continuous shape 14 can be any suitable shape that can be formed that is compliant with these constraints and capable of being generated by the controllable conductive material 12 and/or the actuation control 24 used to set the position and shape of the control-lable conductive material. In an embodiment, continuous shape 14 can be arranged such that portions of the shape do not cross over one another along the path taken from first electrode 16 to second electrode 18. In embodiments, con-tinuous shape 14 can include projections 23 branching off from the portions of continuous shape 14 forming the path from first electrode 16 to second electrode 18. Continuous shape 14 can be defined, for example, using a set of pixels 20 in array 22 to be used to define the continuous shape 14, and/or using vector geometry to define the shape, and then translating the shape to define the set of pixels 20 in array 22 to be used to define the continuous shape 14.

In the embodiment shown in FIG. 1, the controllable conductive material 12 is included in an array 22 of pixels 20. Each pixel 20 can contain controllable conductive material 12 that can be arranged to form a portion of continuous shape 14, with the continuous shape 14 being made of controllable conductive material 12 in each of a plurality of the pixels 22 forming the continuous shape 14.

Figure 2:
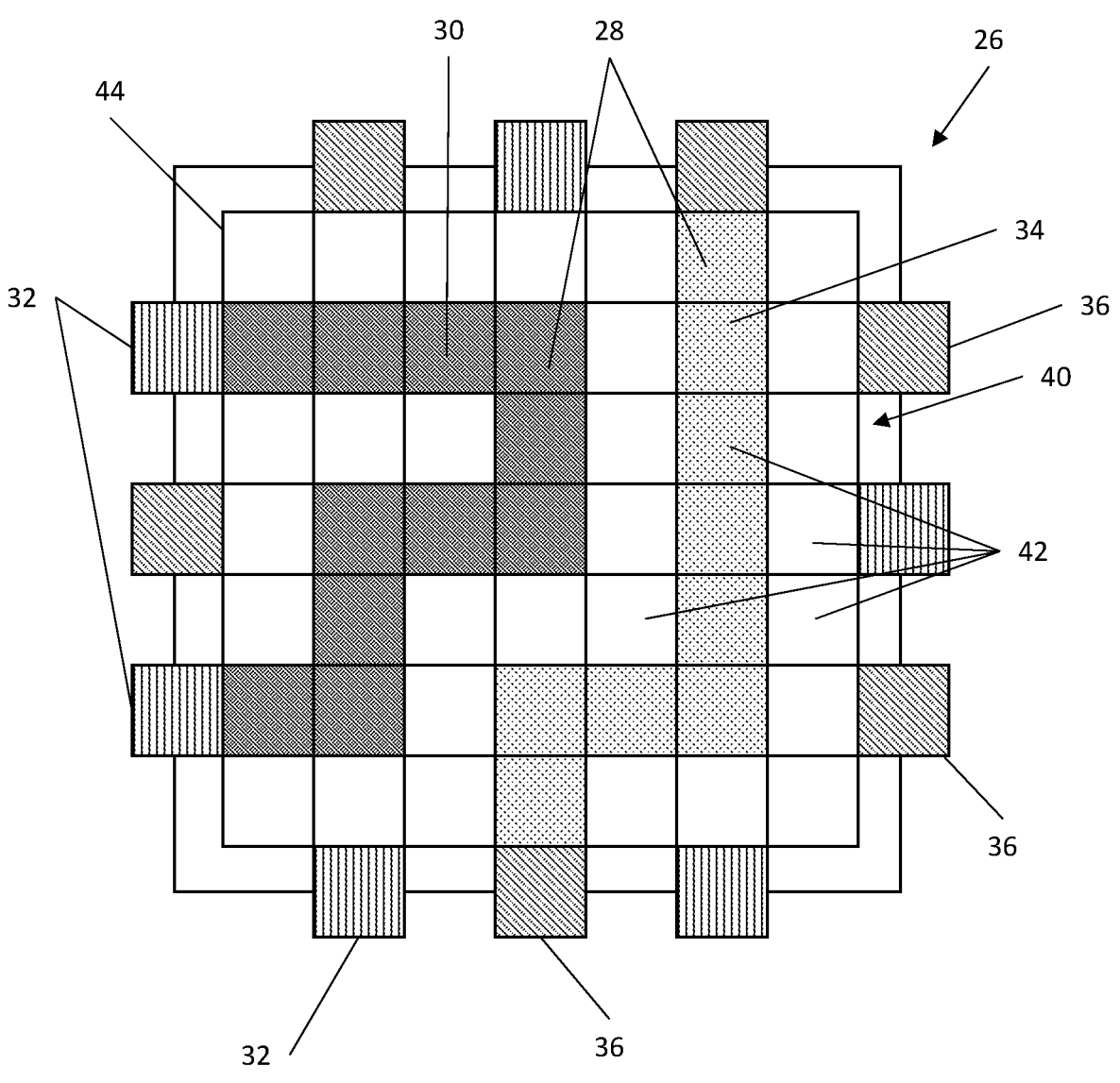
FIG. 2 shows a schematic of an antenna array according to an embodiment.

FIG. 2 shows a schematic of an antenna array 26 according to an embodiment. In the embodiment shown in FIG. 2, controllable conductive material 28 is positioned and shaped to form a first antenna 30 (shown in FIG. 2 as heavy shading) connecting two or more of the transmit circuit electrodes 32 (shown in FIG. 2 using vertical shading lines). The controllable conductive material 28 is also shaped to form a second antenna 34 (shown in FIG. 2 as light shading) connecting two or more of the receive circuit electrodes 36 (shown in FIG. 2 using diagonal shading lines). These additional electrodes can be, for example, distributed around a perimeter of the array 40 of pixels 42 of the controllable conductive material 28. The controllable conductive material 28 can be arranged into first antenna 30 and second antenna 34 using the actuation control 44.

First antenna 30 is a continuous shape formed of the controllable conductive material 28. The continuous shape of first antenna 30 electrically connects two or more transmit circuit electrodes 32. First antenna 30 can serve as a transmit antenna for a signal generated by a transmit circuit such as transmit circuit 62 described below and shown in FIG. 3. In an embodiment, first antenna 30 can be used to transmit a signal in the radio or microwave frequency range into a target containing an analyte to be detected. The signal can be, for example, in the range between radio or microwave frequency range is between about 10 kHz to about 100 GHz. In an embodiment, the first antenna 30 can be used to transmit a signal or plurality of signals sweeping across a range of frequencies.

Transmit circuit electrodes 32 electrically connect first antenna 30 to a transmit circuit such as the transmit circuit 62 discussed below and shown in FIG. 3. The transmit circuit can generate a signal for transmission by first antenna 30. The signal can be generated by any suitable means for generating a signal in the radio or microwave frequency range. The signal generated by the transmit circuit is provided to first antenna 30 by way of the transmit circuit electrodes 32 and 32. The transmit circuit electrodes 32 can be positioned at any suitable point on or around array 40 such that at least some of the controllable conductive material 28 can form the first antenna 30 electrically connecting any two or more of the transmit circuit electrodes 32.

Second antenna 34 is a continuous shape formed from some of the controllable conductive material 28. Second antenna 34 electrically connects at least two receive circuit electrodes 36. The second antenna 34 can be configured to serve as a receive antenna obtaining a signal. The signal obtained by second antenna 34 can be a response to the transmission of the transmit signal at the first antenna 30. In an embodiment, first antenna 30 and second antenna 34 can be formed at separate times. In an embodiment, both first antenna 30 and second antenna 34 can exist simultaneously when formed for overlapping periods of time. When first antenna 30 and second antenna 34 are formed during overlapping periods of time, the second antenna 34 can be shaped with respect to first antenna 30 such that it does not contact or cross first antenna 30.

Receive circuit electrodes 36 electrically connect second antenna 34 to a receive circuit configured to receive and interpret the signal that is obtained at second antenna 34. The receive circuit can be, for example, the receive circuit 64 discussed below and shown in FIG. 3. The receive circuit electrodes 36 can be positioned at any suitable point on or around array 40 such that at least some of the controllable conductive material 28 can form the second antenna 34 electrically connecting any two or more of the receive circuit electrodes 36. In an embodiment, the receive circuit electrodes 36 and the transmit circuit electrodes 32 can be distributed around array 40 such that the receive circuit electrodes 36 and transmit circuit electrodes 32 alternate.

The array 40 when including the first antenna 30 and the second antenna 34 can be used to respectively transmit a signal into a target and obtain a response. This can be incorporated into a non-invasive analyte sensor system using the transmitted signal and obtained response to detect the presence and/or amount of one or more analytes of interest in a target.

Figure 3:
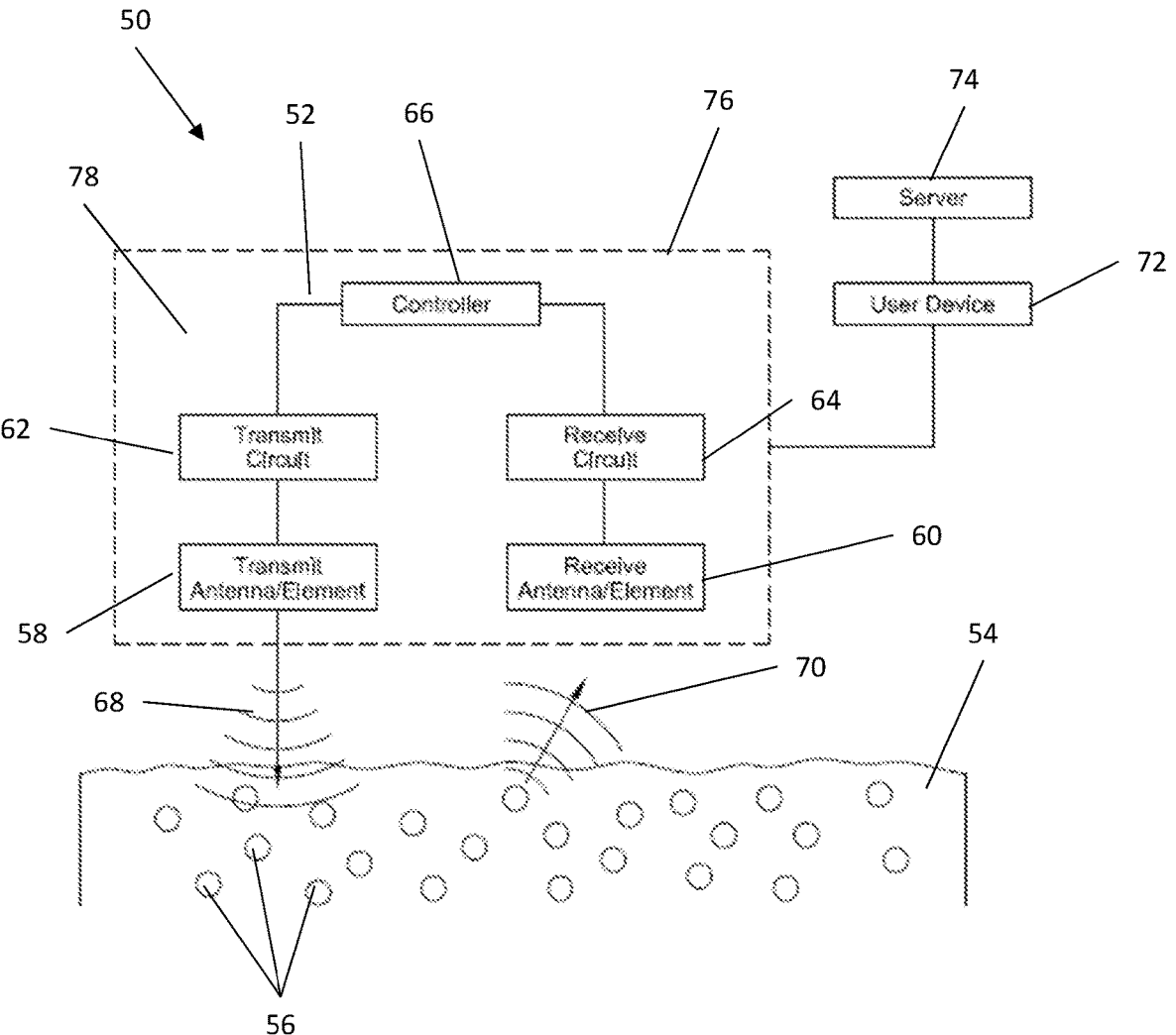
FIG. 3 shows a non-invasive analyte sensor system according to an embodiment.

A non-invasive analyte sensor system according to an embodiment is shown in FIG. 3. The non-invasive analyte sensor system 50 includes non-invasive analyte sensor 52. The sensor 52 is depicted relative to a target 54 that contains an analyte of interest 56. In this example, the sensor 52 is depicted as including an antenna array that includes a transmit antenna/element 58 (hereinafter "transmit antenna 58") and a receive antenna/element 60 (hereinafter "receive antenna 60"). The sensor 52 further includes a transmit circuit 62, a receive circuit 64, and a controller 66. As discussed further below, the sensor 52 can also include a power supply, such as a battery (not shown in FIG. 1).

The transmit antenna 58 is positioned, arranged and configured to transmit a signal 68 that is the radio frequency (RF) or microwave range of the electromagnetic spectrum into the target 54. The transmit antenna 58 can be an antenna having a continuous shape formed of a controllable conductive material. In an embodiment, where receive antenna 60 is an antenna having a continuous shape formed of a controllable conductive material, transmit antenna 58 can be an antenna having a fixed shape. The transmit antenna 58 can be an antenna 10 as shown in FIG. 1 and described above, or first antenna 30 as shown in FIG. 2 and described above. The transmit antenna 58 can have any arrangement and orientation relative to the target 54 that is sufficient to allow the analyte sensing to take place. In one non-limiting embodiment, the transmit antenna 58 can be arranged to face in a direction that is substantially toward the target 54. In an embodiment, transmit antenna 58 can be used to transmit a plurality of signals 68 at varying frequencies, for example to provide a frequency sweep. In an embodiment, when the transmit antenna 58 transmits a plurality of signals 68, the transmit antenna can use a different shape for transmission of one or more of the plurality of signals.

The signal 68 transmitted by the transmit antenna 58 is generated by the transmit circuit 62 which is electrically connectable to the transmit antenna 58. The transmit circuit 62 can be connected to the transmit antenna 58 by way of electrodes at opposing ends of the continuous shape of the transmit antenna 58. The transmit circuit 62 can have any configuration that is suitable to generate a transmit signal to be transmitted by the transmit antenna 58. Transmit circuits for generating transmit signals in the RF or microwave frequency range are well known in the art. In one embodiment, the transmit circuit 62 can include, for example, a connection to a power source, a frequency generator, and optionally filters, amplifiers or any other suitable elements for a circuit generating an RF or microwave frequency electromagnetic signal. In an embodiment, the signal generated by the transmit circuit 62 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 62 can be configured to sweep through a range of frequencies that are within the range of about 10 kHz to about 100 GHz, or in another embodiment a range of about 300 MHz to about 6000 MHz. In an embodiment, the transmit circuit 62 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 60 is positioned, arranged, and configured to detect one or more electromagnetic response signals 70 that result from the transmission of the transmit signal 68 by the transmit antenna 58 into the target 54 and impinging on the analyte 56. The receive antenna 60 can be a continuous shape formed of a controllable conductive material. For example, the receive antenna 60 can be an antenna 10 as shown in FIG. 1 and described above, or second antenna 34 as shown in FIG. 2 and described above. In an embodiment, the receive antenna 60 can be formed in an antenna array along with the transmit antenna 58, for examples as shown in FIG. 2 and described above. In an embodiment, the receive antenna 60 is formed separately from the transmit antenna 58, such as on a separate device including controllable conductive material. In an embodiment, only one of transmit antenna 58 or receive antenna 60 is formed of a controllable conductive material, with the other of transmit antenna 58 or receive antenna 60 being an antenna having a fixed shape, for example an electrode having a fixed shape. In an embodiment, the receive antenna 60 is configured to detect electromagnetic signals having at least two frequencies, each of which is in the range from about 10 kHz to about 100 GHz, or in another embodiment a range from about 300 MHz to about 6000 MHz. The receive antenna 60 can have any arrangement and orientation relative to the target 54 that is sufficient to allow detection of the response signal(s) 70 to allow the analyte sensing to take place. In one non-limiting embodiment, the receive antenna 60 can be arranged to face in a direction that is substantially toward the target 54. In an embodiment, the receive antenna 60 can be used to obtain a plurality of response signals 70, for example responses to a frequency sweep being performed with the signals 68 transmitted by transmit antenna 58. In an embodiment, the shape used for the receive antenna 60 can be varied over time when receiving response signals 70. In an embodiment, variation in the shape of receive antenna 60 over time can be based on timing of a frequency sweep of the signals 68 being transmitted at transmit antenna 58.

The receive circuit 64 is electrically connectable to the receive antenna 60 and conveys the received response from the receive antenna 60 to the controller 66. The receive circuit 64 can have any configuration that is suitable for interfacing with the receive antenna 60 to convert the electromagnetic energy detected by the receive antenna 60 into one or more signals reflective of the response signal(s) 70. The construction of receive circuits are well known in the art. The receive circuit 64 can be configured to condition the signal(s) prior to providing the signal(s) to the controller 66, for example through amplifying the signal(s), filtering the signal(s), or the like. Accordingly, the receive circuit 64 may include filters, amplifiers, or any other suitable components for conditioning the signal(s) provided to the controller 66. In an embodiment, at least one of the receive circuit 64 or the controller 66 can be configured to decompose or demultiplex a complex signal, detected by the receive antenna 60, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 66 controls the operation of the sensor 52. The controller 66, for example, can direct the transmit circuit 62 to generate a transmit signal to be transmitted by the transmit antenna 58. The controller 66 further receives signals from the receive circuit 64. The controller 66 can optionally process the signals from the receive circuit 64 to detect the analyte(s) 56 in the target 54. In one embodiment, the controller 66 may optionally be in communication with at least one external device 72 such as a user device and/or a remote server 74, for example through one or more wireless connections such as Bluetooth, wireless data connections such a 4G, 5G, LTE or the like, or Wi-Fi. If provided, the external device 72 and/or remote server 74 may process (or further process) the signals that the controller 66 receives from the receive circuit 64, for example to detect the analyte(s) 56. If provided, the external device 72 may be used to provide communication between the sensor 52 and the remote server 74, for example using a wired data connection or via a wireless data connection or Wi-Fi of the external device 72 to provide the connection to the remote server 74. Controller 66, external device 72, and/or remote server 74 can be configured to determine the shapes for at least one of transmit antenna 58 and/or receive antenna 60.

With continued reference to FIG. 3, the sensor 52 may include a sensor housing 76 (shown in dashed lines) that defines an interior space 78. Components of the sensor 52 may be attached to and/or disposed within the housing 76. For example, the transmit antenna 58 and the receive antenna 60 are attached to the housing 76. In some embodiments, the antennas 58, 60 may be entirely or partially within the interior space 78 of the housing 76. In some embodiments, the antennas 58, 60 may be attached to the housing 76 but at least partially or fully located outside the interior space 78. In some embodiments, the transmit circuit 62, the receive circuit 64 and the controller 66 are attached to the housing 76 and disposed entirely within the sensor housing 76.

If receive antenna 60 is formed during a time overlapping with transmission of signal 68 by transmit antenna 58, receive antenna 60 can be decoupled or detuned with respect to the transmit antenna 58 such that electromagnetic coupling between the transmit antenna 58 and the receive antenna 60 is reduced. The decoupling of the transmit antenna 58 and the receive antenna 60 increases the portion of the signal(s) detected by the receive antenna 60 that is the response signal(s) 70 from the target 54, and minimizes direct receipt of the transmitted signal 68 by the receive antenna 60.

In an embodiment, coupling between the transmit antenna 58 and the receive antenna 60 is 95% or less. In another embodiment, coupling between the transmit antenna 58 and the receive antenna 60 is 90% or less. In another embodiment, coupling between the transmit antenna 58 and the receive antenna 60 is 85% or less. In another embodiment, coupling between the transmit antenna 58 and the receive antenna 60 is 75% or less.

Any technique for reducing coupling between the transmit antenna 58 and the receive antenna 60 can be used. For example, the decoupling between the transmit antenna 58 and the receive antenna 60 can be achieved by the selection of the continuous shape of the controllable conducive material that is used for transmit antenna and/or receive antenna 60. For example, the decoupling of the transmit antenna 58 and the receive antenna 60 can be achieved by controlling the shape of at least one of the transmit antenna 58 and the receive antenna 60 such that the transmit antenna 58 and receive antenna 60 have different geometries from one another.

Control of the shape of the transmit antenna 58 and/or the receive antenna 60 can further be used to manipulate the spacing between each antenna 58, 60 such that the antennas 58, 60 are decoupled, forcing a proportion of the electromagnetic lines of force of the transmitted signal 68 into the target 54 thereby minimizing or eliminating as much as possible direct receipt of electromagnetic energy by the receive antenna 60 directly from the transmit antenna 58 without traveling into the target 54. The appropriate spacing between each antenna 58, 13 can be determined based upon factors that include, but are not limited to, the output power of the signal from the transmit antenna 58, the size of the antennas 58, 60, the frequency or frequencies of the transmitted signal, and the presence of any shielding between the antennas. The spacing of the antennas 58, 60 can be determined based on, for example, selecting different shapes and positions of the antennas 58, 60 and analyzing data obtained from transmitting and receiving signals in these varied configurations of shape and position. This technique helps to ensure that the response detected by the receive antenna 60 is measuring the analyte 56 and is not just the transmitted signal 68 flowing directly from the transmit antenna 58 to the receive antenna 60. In some embodiments, the spacing between the antennas 58, 60 can be used together with control of the shapes used for of the antennas 58, 60 to achieve decoupling.

In one embodiment, the transmit signal that is transmitted by the transmit antenna 58 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

Figure 4:
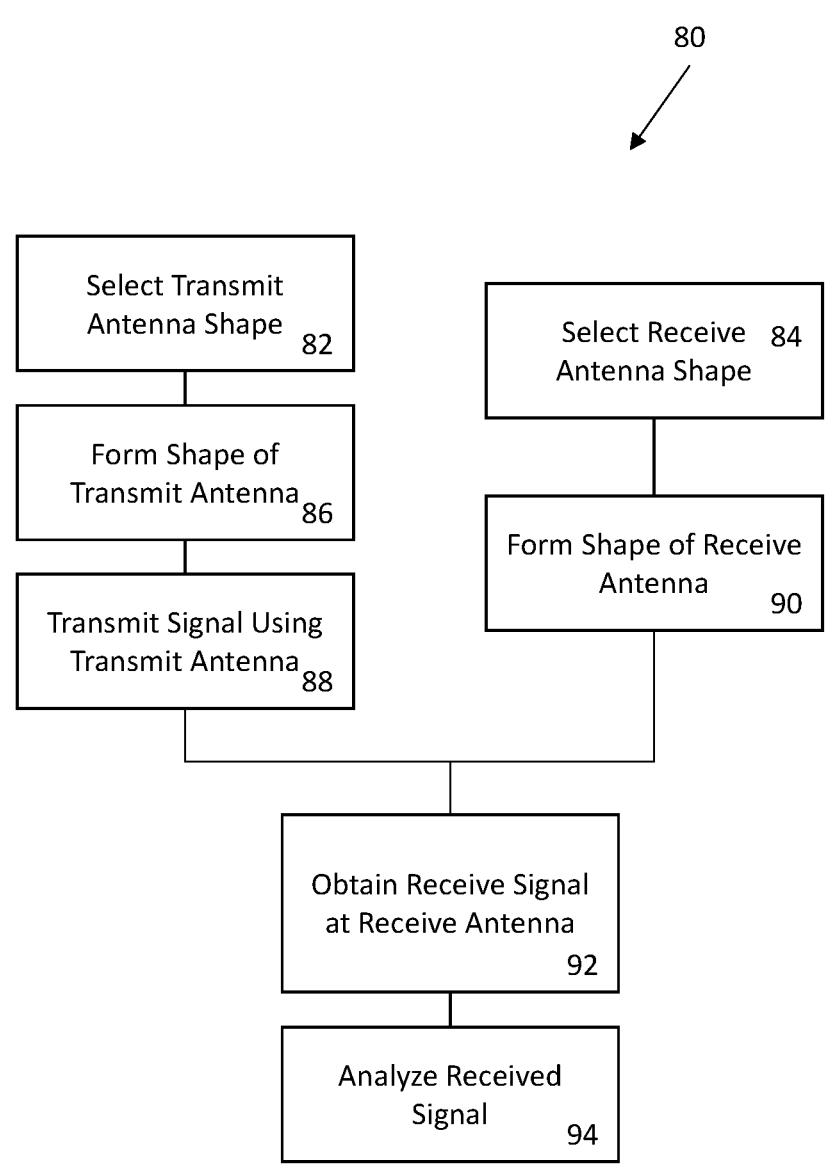
FIG. 4 shows a flowchart of a method for detecting an analyte using a shape-changing antenna according to an embodiment.

FIG. 4 shows a flowchart of a method for detecting an analyte using a shape-changing antenna according to an embodiment. Method 80 includes selecting a shape for the transmit antenna 82, selecting a shape for the receive antenna 84, forming the transmit antenna 86, transmitting the transmit signal using the transmit antenna 88, forming the receive antenna 90, and obtaining a receive signal by way of the receive antenna 92. The signal obtained by the receive antenna fan further be analyzed to determine the presence or amount of one or more analytes 94. In an embodiment, method 80 can be performed using a system including antenna formed from controllable conductive material, for example, one or more antennas according to antenna 10 shown in FIG. 1 and described above, or an antenna array according to antenna array 26 shown in FIG. 2.

A shape is selected for the transmit antenna at 82. The shape can be any continuous shape from one electrode connected to a transmit circuit to another electrode connected to the transmit circuit. In an embodiment, the shape can be arranged such that it does not cross over itself or provide any positions where a short may occur. In an embodiment, the shape can be selected at 82 from a library of predetermined shapes. In an embodiment, the shape can be selected at 82 by procedurally generating a suitable shape. In an embodiment, the shape can be selected at 82 based on the analyte of interest in the detection performed in method 80. In an embodiment, the shape can be selected based on effectiveness data. As a non-limiting example, the shape can be selected based on effectiveness data associated with the shape and an analyte of interest to be detected in the performance of method 80. In an embodiment, the shape can be selected based on procedural generation according to parameters based on effectiveness in detecting or measuring an analyte of interest to be detected in the performance of method 80.

A shape is selected for the receive antenna at 84. The shape can be any continuous shape from one electrode connected to a receive circuit to another electrode connected to the receive circuit. In an embodiment, the shape can be arranged such that it does not cross over itself or provide any positions where a short may occur. In an embodiment, the shape can be selected at 84 from a library of predetermined shapes. In an embodiment, the shape can be selected at 84 by procedurally generating a suitable shape. In an embodiment, the shape can be selected at 84 based on the analyte of interest in the detection performed in method 80. In an embodiment, the shape can be selected based on effectiveness data. As a non-limiting example, the shape can be selected based on effectiveness data associated with the shape and an analyte of interest to be detected in the performance of method 80. In an embodiment, the shape can be selected based on procedural generation according to parameters based on effectiveness in detecting or measuring an analyte of interest to be detected in the performance of method 80. In an embodiment, the shape for the receive antenna can further be based on a shape of the transmit antenna selected at 82. For example, this may be based on associations between transmit antenna shapes and receive antenna shapes, or parameters for procedural generation that account for characteristics of the transmit antenna, for example parameters for procedural generation of the receive antenna configured to ensure particular distances between the transmit and receive antennas.

The shape selected for the transmit antenna is formed at 86. The shape for the transmit antenna can be formed by arranging controllable conductive material in the shape selected at 82. The arrangement of the controllable conductive material can be through any suitable manipulation of the conductive material in a configurable antenna device. For example, the shape can be formed through mechanical, magnetic, electromagnetic, or any other suitable manipulation of the controllable conductive material. The formation of the shape at 86 provides an antenna extending continuously from a first electrode connected to a transmit circuit to a second electrode connected to the transmit circuit, such that a signal provided by the transmit circuit can be transmitted by the antenna. A transmit signal is transmitted using the transmit antenna at 88. The transmit circuit generates a signal which travels through the circuit formed by the first electrode connected to the transmit circuit, the transmit antenna formed by the controllable conductive material, and the second electrode, resulting in the transmit signal being transmitted by the transmit antenna. The transmit signal can be a transmit signal suitable for use in detection of an analyte. In an embodiment, the transmit signal can include at least two frequencies in the microwave range. with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The transmit signal can be transmitted into a target in which the analyte of interest is to be detected, for example due to proximity or orientation of the target relative to the configurable antenna device in which the transmit antenna is formed.

The receive antenna is formed at 90. The receive antenna can be formed by arranging controllable conductive material to the shape determined at 84. The arrangement of the controllable conductive material can be through any suitable manipulation of the conductive material in a configurable antenna device. For example, the shape can be formed through mechanical, magnetic, electromagnetic, or any other suitable manipulation of the controllable conductive material. The controllable conductive material can be controllable conductive material included in the configurable antenna device in which the transmit antenna is formed at 86, or another configurable antenna device separate from the controllable antenna device in which the transmit antenna is formed at 86. In an embodiment, the receive antenna is formed at 90 prior to the formation of the transmit antenna at 86. In an embodiment, the receive antenna is formed during a period of time that overlaps with the formation of the transmit antenna at 86 and/or transmission of the transmit signal at 88. In an embodiment, the formation of the transmit antenna at 86 and the formation of the receive antenna at 90 can be performed sequentially. In an embodiment, the receive antenna is formed following the transmission of the transmit signal at 88. The receive antenna can be used to obtain a receive signal at 92. The receive antenna formed at 90 forms a circuit with a receive circuit by way of first and second electrodes that the receive circuit extends between. The receive signal can be a signal from the target into which the transmit signal was transmitted at 88. The receive signal can include components at various frequencies. The receive signal obtained by the receive antenna at 92 can include at least two frequencies, each of which is in the range from about 10 kHz to about 100 GHz, or in another embodiment a range from about 300 MHz to about 6000 MHz. The receive signal can be analyzed to determine the presence of one or more analytes at 94. In an embodiment, the analysis of the receive signal can be performed at a device including the receive circuit. In an embodiment, the analysis can be performed at an external device such as external device 72 described above and shown in FIG. 3. In an embodiment, the analysis can be performed at a server such as server 74 described above and shown in FIG. 3. The analysis can indicate a presence and/or an amount of the analyte in the target, based on the characteristics of the transmit signal and the resulting response signal.

Figure 5:
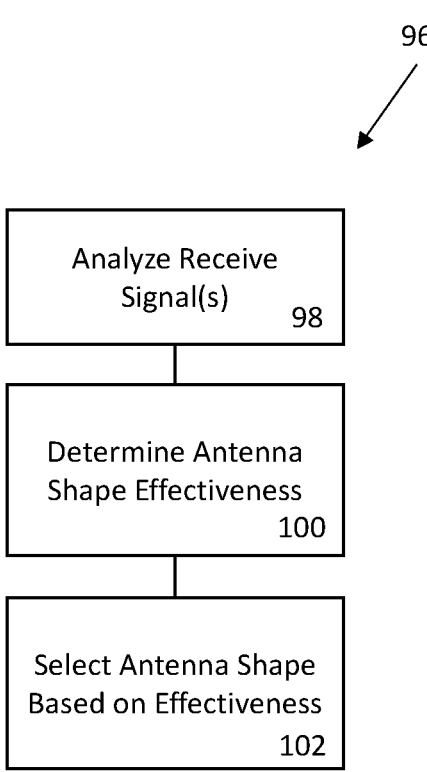
FIG. 5 shows a flowchart of a method for determining an antenna shape to use in detection of an analyte.

FIG. 5 shows a flowchart of a method for determining effectiveness of an antenna shape in detection of an analyte. Method 96 can follow one or more iterations of method 80 shown in FIG. 4 and described above. Method 96 can include analyzing one or more receive signals 98, determining an effectiveness for one or both of the transmit antenna shape or the receive antenna shape 100, and optionally further selecting a shape for one or both of the transmit antenna shape or the receive antenna shape based on the determined effectiveness 102. One or more receive signals can be analyzed at 98. The receive signals analyzed at 98 can be analyzed to determine presences or amounts of an analyte of interest according to the transmission and receipt of signals by transmit and/or receive antennas having particular shapes formed of controllable conductive material. The results can be associated with the shapes and/or positions used for the transmit and/or receive antennas in that measurement. In an embodiment, the positions of the antennas associated with the analyzed signals can be a relative measure such as spacing between the transmit and receive antennas. In an embodiment, the positions of the antennas associated with the analyzed signals can be particular positions of one or both of the transmit and receive antennas in an antenna array when the transmit and/or receive antennas are formed using the controllable conductive material. An effectiveness for one or both of the transmit antenna shape or the receive antenna shape is determined at 100. In an embodiment, the effectiveness is based on an accuracy of the analysis results for the signal obtained using the transmit antenna shape and/or the receive antenna shape compared to a reference value, such as a value obtained by another measurement method, a known composition of the target, or the like. In an embodiment, the effectiveness is based on stability of the analysis results over time, uncertainty values for the analysis results, measurements or estimates in noise, signal to noise ratio, or any other suitable characteristic of the analysis results themselves. In an embodiment, the effectiveness obtained at 100 can be used to select shapes and/or positions for one or both of the transmit antenna shape or the receive antenna shape at 102. The effectiveness can, for example, be used to select particular predetermined shapes, select parameters used in the procedural generation of antenna shapes, as discussed above with respect to steps 82 and 84 of method 80, shown in FIG. 4 and described above.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A non-invasive analyte sensor system comprising a controllable antenna configured to form a transmit shape and to form a receive shape, the controllable antenna configured to transmit a signal into a target using the transmit shape and to obtain a receive signal using the receive shape.

2. The non-invasive analyte sensor system of claim 1, wherein the controllable antenna is configured to provide the transmit shape during a first period of time and the receive shape during a second period of time.

3. The non-invasive analyte sensor system of claim 2, wherein the first period of time overlaps with the second period of time.

4. The non-invasive analyte sensor system of claim 2, wherein the first period of time does not overlap with the second period of time.

5. The non-invasive analyte sensor system of claim 4, wherein the second period of time begins when the first period of time ends.

6. The non-invasive analyte sensor system of claim 1, wherein the controllable antenna is configured to switch between the transmit shape and the receive shape.

\*  \*  \*  \*  \*